(12) United States Patent
Reinke

(10) Patent No.: US 6,240,582 B1
(45) Date of Patent: Jun. 5, 2001

(54) APPARATUS FOR POSITIONING A PATIENT-SUPPORT DECK

(75) Inventor: Christian H. Reinke, Wilmington, OH (US)

(73) Assignee: Hill-Rom, Inc., Batesville, IN (US)

( * ) Notice: Subject to any disclaimer, the term of this patent is extended or adjusted under 35 U.S.C. 154(b) by 0 days.

(21) Appl. No.: 09/365,334

(22) Filed: Jul. 30, 1999

(51) Int. Cl.$^7$ .............................. A61B 6/04; A61G 13/00
(52) U.S. Cl. ................................. 5/601; 378/209
(58) Field of Search .................. 5/601, 613, 614; 378/177, 209; 108/143

(56) References Cited

U.S. PATENT DOCUMENTS

| | | |
|---|---|---|
| 2,605,151 | 7/1952 | Shampaine . |
| 3,588,500 * | 6/1971 | Koerner ..................................... 5/601 |
| 3,868,103 * | 2/1975 | Pageot et al. ............................. 5/614 |
| 3,980,288 | 9/1976 | Mitchell et al. . |
| 4,013,019 * | 3/1977 | Horsey .................................. 5/601 X |
| 4,061,324 | 12/1977 | Kvaerna et al. . |
| 4,327,596 | 5/1982 | Simon . |
| 4,700,938 * | 10/1987 | Chambron ................................. 5/601 |
| 4,773,637 * | 9/1988 | Jarin ..................................... 5/601 X |
| 4,989,848 | 2/1991 | Monroe . |
| 5,469,588 | 11/1995 | DiMatteo et al. . |
| 5,490,297 | 2/1996 | Bradcovich et al. . |
| 5,659,909 * | 8/1997 | Pfeuffer et al. ....................... 5/613 X |

* cited by examiner

*Primary Examiner*—Michael F. Trettel
(74) *Attorney, Agent, or Firm*—Bose McKinney & Evans LLP

(57) ABSTRACT

A patient-support apparatus that comprises a base, a patient-support deck having a longitudinal length and a transverse width, and a deck-positioning assembly coupling the patient-support deck to the base. The patient-support deck is supported with respect to the deck-positioning assembly for longitudinal movement. The deck-positioning assembly includes an actuator having a first portion and a second portion that moves transversely relative to the first portion. The deck-positioning assembly includes a transmission assembly configured to convert transverse movement of the second portion relative to the first portion into longitudinal movement of the patient-support deck relative to the base.

43 Claims, 8 Drawing Sheets

APPARATUS FOR POSITIONING A PATIENT-SUPPORT DECK

BACKGROUND AND SUMMARY OF THE INVENTION

The present invention relates to an apparatus for positioning a patient-support deck and particularly, to an apparatus that moves a patient-support deck longitudinally relative to a base of a patient-support device. More particularly, the present invention relates to an apparatus for longitudinally moving a patient-support deck to facilitate taking x-ray or fluoroscopic images of a patient resting on a mattress supported by the patient-support deck.

Many conventional patient-support devices, such as operating tables and imaging tables, have mechanisms that are used to move a patient-support deck of the device longitudinally relative to a base of the device. Such adjustments in the longitudinal position of the patient-support deck may be made so that x-rays or fluoroscopic images can be taken of a patient supported by the patient-support deck. Some X-ray devices and other types of imaging devices have C-arms that are movable to positions having portions of the C-arm above and below the patient-support deck. Thus, it is desirable for patient-support devices to have a minimum amount of structure in the area beneath the patient-support deck to minimize the interference of the structure with the C-arm.

In accordance with one embodiment of the present invention, a patient-support apparatus includes a base, a patient-support deck that has a longitudinal length and a transverse width, and a deck-positioning assembly coupling the patient-support deck to the base. The patient-support deck is supported with respect to the deck-positioning assembly for longitudinal movement. Additionally, the deck-positioning assembly includes an actuator having a first portion and a second portion that moves transversely relative to the first portion. Furthermore, the deck-positioning assembly includes a transmission assembly configured to convert transverse movement of the second portion relative to the first portion into longitudinal movement of the patient-support deck relative to the base.

In preferred embodiments, the actuator is a linear actuator, such as a hydraulic cylinder, and the second portion moves axially along a first transverse axis relative to the first portion. Also in preferred embodiments, the transmission assembly includes a threaded shaft and a ball nut coupled to the threaded shaft. The threaded shaft is rotatable about a second transverse axis and the linear actuator is coupled to the ball nut so that extension and retraction of the second portion of the linear actuator relative to the first portion moves the ball nut along the threaded shaft which causes the threaded shaft to rotate. Also in preferred embodiments, the transmission assembly includes a pinion coupled to the threaded shaft and a rack coupled to the patient-support deck. The pinion engages the rack such that rotation of the threaded shaft and pinion causes longitudinal movement of the rack and patient-support deck relative to the base.

In accordance with another embodiment of the present invention, a patient-support apparatus includes a base, a patient-support deck having a longitudinal length and a transverse width, and a deck-positioning assembly coupling the patient-support deck to the base. The patient-support deck is supported with respect to the deck-positioning assembly for longitudinal movement. The deck-positioning assembly includes a shaft rotatable about a transverse axis between a first position and a second position. A rack is coupled to the patient-support deck and a lock assembly is coupled to the shaft. The lock assembly includes a member that moves in response to rotation of the shaft. The member engages the rack when the shaft is in the first position to prevent longitudinal movement of the patient-support deck relative to the base. The member is disengaged from the rack when the shaft is in the second position to allow longitudinal movement of the patient-support deck relative to the base.

In preferred embodiments, an actuator, such as an electric solenoid, is provided for moving the shaft between the first and second positions. Also in preferred embodiments, the member of the lock assembly is a pawl. One preferred lock assembly includes a cam coupled to the shaft and engaging the pawl so that rotation of the shaft rotates the cam to move the pawl into and out of engagement with the rack. After the lock assembly is unlocked, the patient-support deck is manually movable relative to the base. Also in preferred embodiments, an angle sensor is coupled to the deck positioning assembly. If the angle sensor indicates that the patient-support deck is in a non-horizontal position, then the actuator is disabled preventing the lock assembly from being unlocked.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
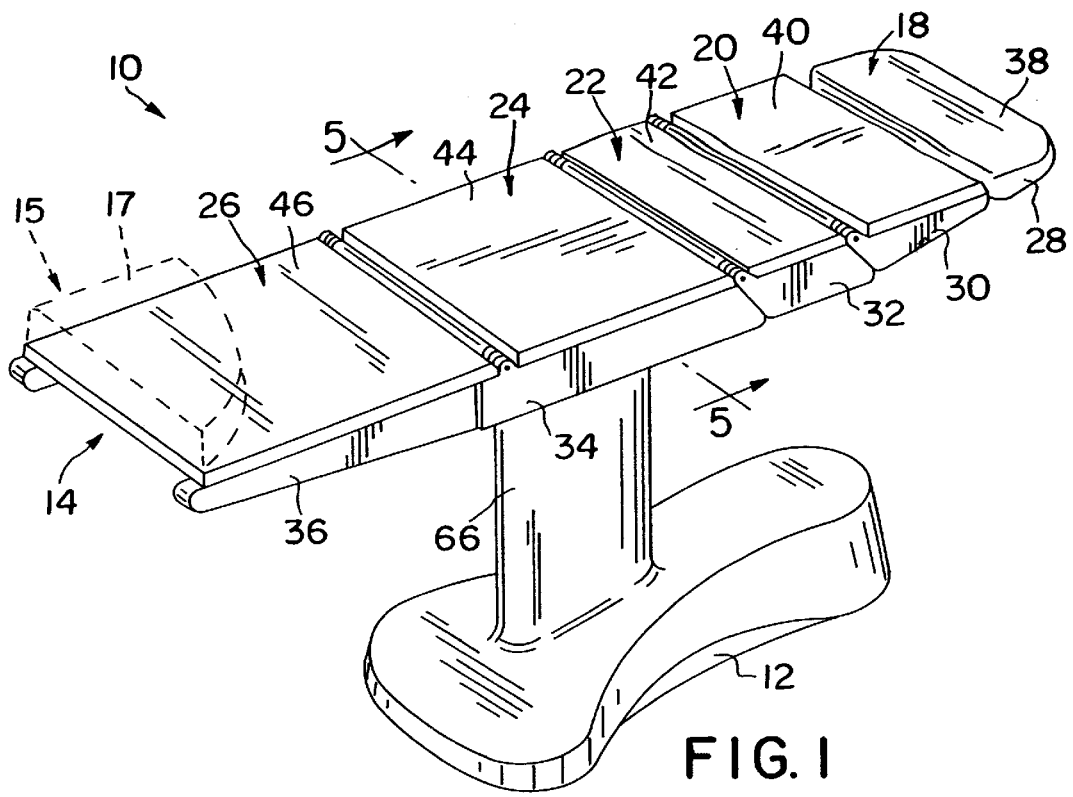
FIG. 1 is a perspective view of a patient-support apparatus in accordance with the present invention showing a patient-support deck having a plurality of articulated deck sections arranged in coplanar relation, a base beneath the patient-support deck, and a cosmetic cover overlying the base and shrouding a deck-positioning assembly which couples the patient-support deck to the base.
Figure 2:
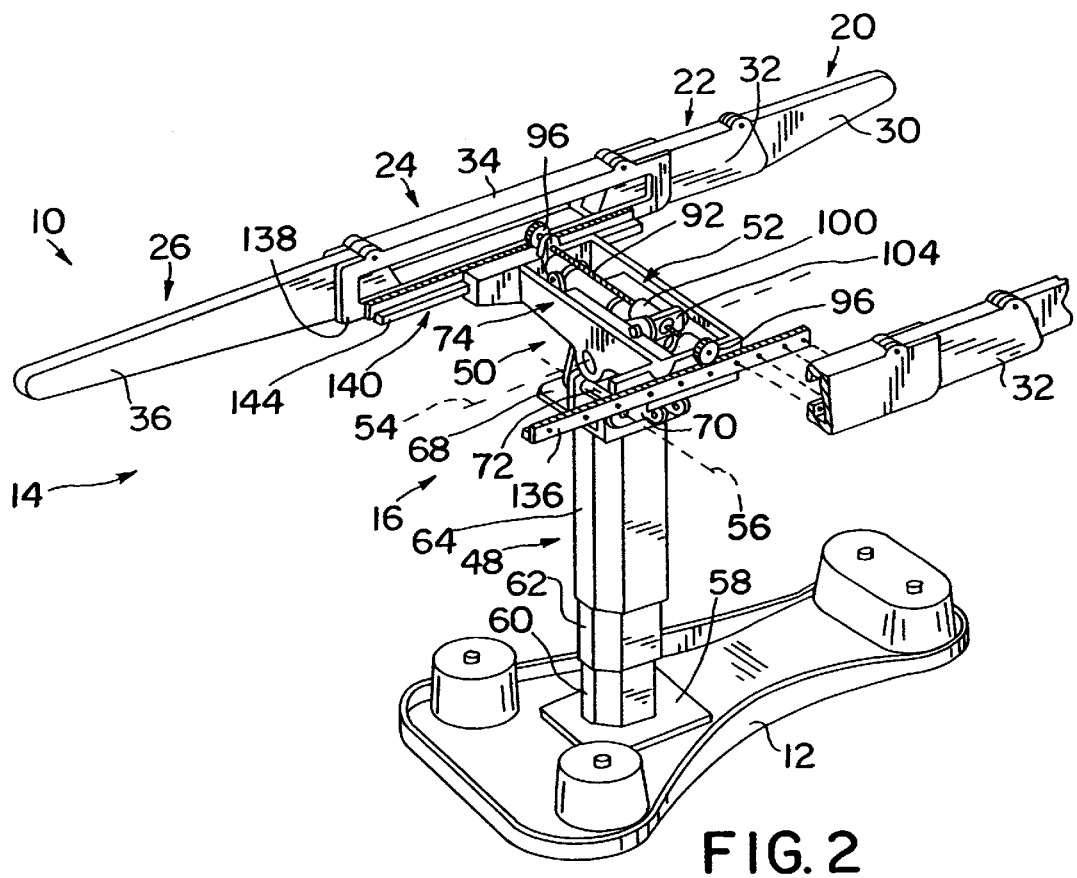
FIG. 2 is a perspective view of the patient-support apparatus of FIG. 1, with portions broken away, showing the deck-positioning assembly including a hi/lo mechanism extending vertically upwardly from the base, a tilt/trend mechanism situated atop the hi/lo mechanism, and a deck-slide mechanism coupling the tilt/trend mechanism to the patient-support deck.

A patient-support apparatus 10, such as an operating table or an imaging table, includes a base 12 and a patient-support deck 14 supported relative to base 12 as shown in FIG. 1. A mattress 15, a portion of which is shown in FIG. 1 (in phantom), includes an upwardly facing patient-support surface 17 and is supported by deck 14. A deck-positioning assembly 16 is coupled to base 12 and is coupled to deck 14 as shown in FIG. 2. Deck-positioning assembly 16 includes a hi/lo mechanism 48, a tilt/trend mechanism 50, and a deck-slide mechanism 52 as shown in FIG. 2. The present invention relates to features of deck-slide mechanism 52 as discussed below in further detail.

Patient-support deck 14, in the illustrated embodiment, is articulated and has a head section 18, an upper back section 20, a lower back section 22, a seat section 24, and a foot section 26. Sections 18, 20, 22, 24, 26 are serially hinged together for pivoting movement about respective transverse axes. Although illustrative deck 14 includes five deck sections 18, 20, 22, 24, 26, it is within the scope of the invention as presently perceived for deck 14 to have a different number of deck sections and to have deck sections that pivot about axes having orientations other than transverse. An example of an alternative patient-support deck is shown and described in U.S. patent application Ser. No. 09/187,990 which is assigned to the assignee of the present invention and which is hereby incorporated herein by reference.

Deck sections 18, 20, 22, 24, 26 each include frame members 28, 30, 32, 34, 36, respectively, and panels 38, 40, 42, 44, 46, respectively, that are coupled to associated frame members 28, 30, 32, 34, 36. One or more of panels 28, 30, 32, 34, 36 are made from a radiotransluscent material that permits x-rays and rays from fluoroscopic imaging machines to pass therethrough. Deck 14 further includes drive mechanisms (not shown) that operate to articulate sections 18, 20, 22, 26 relative to seat section 24 and relative to base 12.

Illustrative hi/o mechanism 48 operates to raise and lower deck 14 relative to base 12. Tilt/trend mechanism 50 is situated atop hi/lo mechanism 18 and operates to tilt deck 14 side to side about a longitudinal axis 54 and to tilt deck 14 front to rear about a transverse axis 56. Deck-slide mechanism 54 is coupled to tilt/trend mechanism 50 and operates to move deck 14 longitudinally relative to base 12. Thus, articulation of deck sections 18, 20, 22, 26 of patient-support deck 14 and operation of mechanisms 48, 50, 52 of deck-positioning assembly 16 permits patient-support apparatus 10 to be moved into a multitude of configurations for supporting a patient thereon.

Illustrative hi/lo mechanism 48 includes a bottom plate 58 coupled to base 12 and telescoping first, second, and third support tubes 60, 62, 64 situated above plate 58. Mechanism 48 further includes a drive mechanism (not shown) positioned within the interior regions of tubes 60, 62, 64. This drive mechanism operates to extend and retract tubes 60, 62, 64 thereby raising and lowering, respectively, deck 14 relative to base 12. Patient-support apparatus 10 includes a cover 66 that shrouds base 12 and hi/lo mechanism 48. Cover 66 includes telescoping portions (not shown) that extend and retract as tubes 60, 62, 64 extend and retract.

Illustrative tilt/trend mechanism 50 includes a first member 68 coupled to the top end of tube 64. Mechanism 50 further includes a second member 70 coupled to first member 68 for pivoting movement about transverse axis 56. Mechanism 50 includes suitable couplers, such as pivot pin 72 shown in FIG. 2, for coupling members 68, 70 together. Mechanism 50 includes a third member or platform 74 that is coupled to second member 70 for pivoting movement about longitudinal axis 54. Suitable couplers (not shown) are provided for coupling platform 74 and second member 70 together. Mechanism 50 also includes drive mechanisms (not shown) that operate to pivot second member 70 about transverse axis 56 relative to first member 68 and that operate to pivot platform 74 about longitudinal axis 54 relative to second member 70.

It will be appreciated that various mechanical and electromechanical actuators and drivers may be used to raise and lower deck 14 relative to base 12, to tilt deck 14 relative to base 12, and to articulate deck sections 18, 20, 22, 24, 26. It is well known in the art that electric, hydraulic, and pneumatic actuators in combination with various types of transmission elements including lead screw drives and various types of mechanical linkages may be used to create relative movement of portions of patient-support devices. As a result, the term "drive mechanism(s)" is intended to cover all types of mechanical, electromechanical, hydraulic, and pneumatic mechanisms, including manual cranking mechanisms of all types, and including combinations thereof such as hydraulic cylinders in combination with electromechanical pumps for pressuring fluid received by the hydraulic cylinders.

Figure 3:
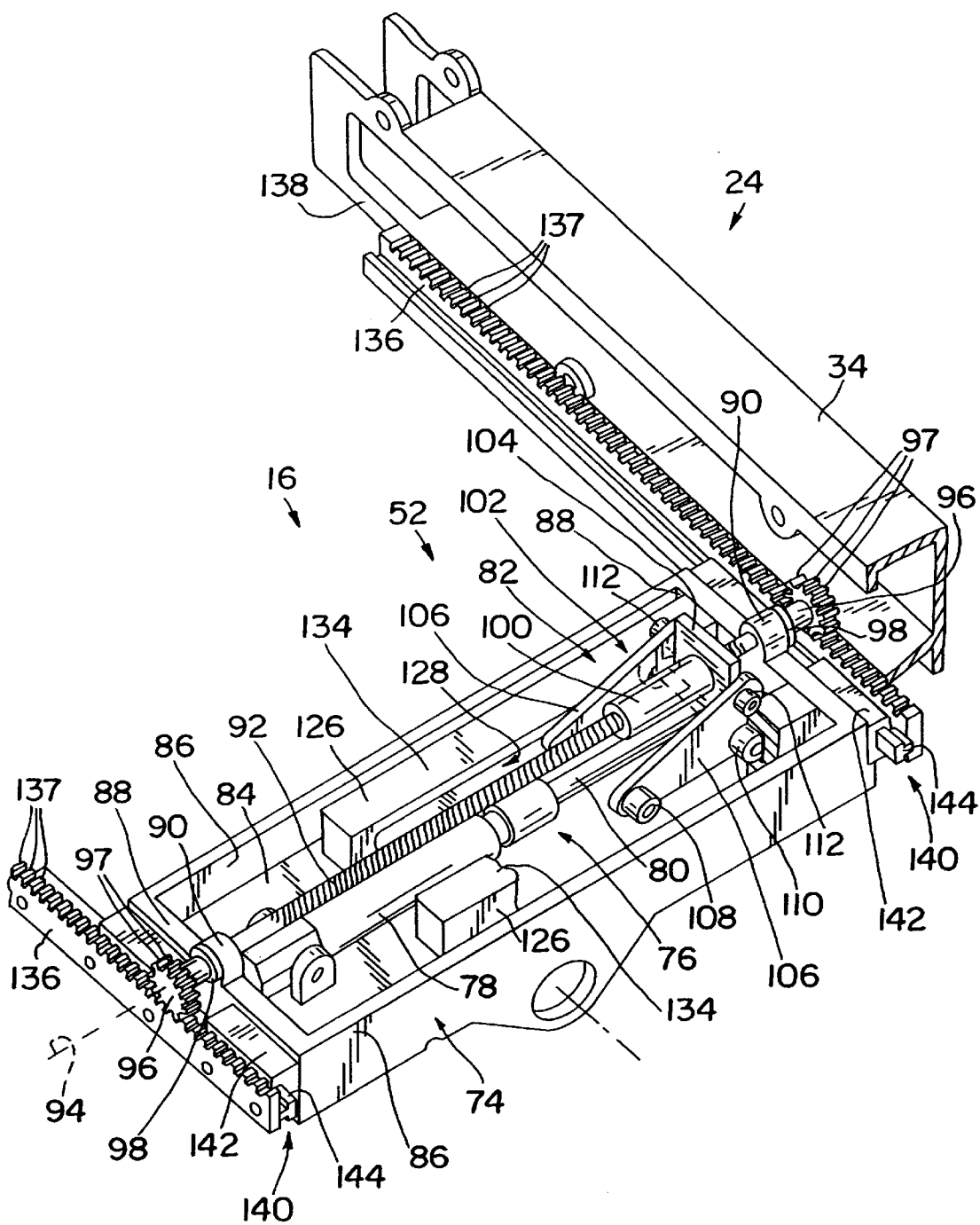
FIG. 3 is an enlarged perspective view of a portion of the patient-support apparatus of FIG. 2, with portions broken away showing a transversely oriented hydraulic cylinder coupled to an upper platform of the tilt/trend mechanism, a threaded shaft supported for rotation about a transverse axis relative to the upper platform, a ball nut coupled to the threaded shaft, a carriage assembly coupling the hydraulic cylinder to the ball nut, a pair of pinions coupled to ends of the threaded shaft, a pair of racks coupled to the seat section of the patient-support deck, and a pair of linear bearings supporting the racks and patient-support deck relative to the upper platform.

Deck-slide mechanism 52 includes an actuator 76, shown for example in FIG. 3, having a first portion 78 and a second portion 80 that moves transversely relative to first portion 78. Mechanism 52 further includes a transmission assembly 82 that converts transverse movement of second portion 80 into longitudinal movement of deck 14. In preferred embodiments, actuator 76 is a hydraulic cylinder (hereinafter referred to as hydraulic cylinder 76) having a housing (hereinafter referred to as housing 78) and a piston rod (hereinafter referred to as piston rod 80). However, it is within the scope of the invention as presently perceived for other types of actuators, such as a pneumatic cylinder or a linear actuator having a lead screw drive driven by an electric motor, to be provided in deck-slide mechanism 52 in lieu of hydraulic cylinder 76.

Platform 74 includes a bottom wall 84, a pair of transversely extending side walls 86 extending upwardly from bottom wall 84, and a pair of longitudinally extending end walls 88 extending upwardly from bottom wall 84 as shown in FIG. 3. Side walls 86 cooperate with end walls 88 to define a compartment above bottom wall 84. A pair of flanges 84 extend upwardly from bottom wall 84 and housing 78 of hydraulic cylinder 76 is coupled to flanges 84 as shown in FIG. 3. Hydraulic cylinder 76 is positioned to lie within the compartment defined by walls 84, 86, 88. Hydraulic fluid is pumped into or extracted from housing 78 in a conventional manner to extend and retract piston rod 80 along a transverse axis 89.

Platform 74 includes a pair of shaft-support flanges 90, each of which extend upwardly from a respective end wall 88 as shown in FIG. 3. Transmission assembly 82 includes a threaded shaft 92 that is supported by flanges 90 for rotation about a transverse axis 94. In preferred embodiments, hydraulic cylinder 76 and shaft 92 are coupled to platform 74 such that axis 94 is parallel with and vertically above axis 89. Shaft 92 is positioned to lie above the compartment defined by walls 84, 86, 88 and end portions of shaft 92 extend outwardly beyond end walls 88 of platform 76. A pair of pinions 96 are coupled to respective end portions of shaft 92. Optionally, a pair of thrust washers or thrust bearings 98 may be provided between pinions 96 and flanges 90. In addition, a pair of radial bearings or bushings (not shown) may be provided to support shaft 92 relative to flanges 90. Of course, a pair of one-piece bushings, each having a thrust portion and a radial portion may also be used as an alternative.

Transmission assembly 82 includes a ball nut 100 coupled to shaft 92 for transverse axial movement along axis 94. Transmission assembly 82 further includes a carriage assembly 102 coupled to ball nut 100 and coupled to piston rod 80 as shown in FIGS. 3–6. Carriage assembly 102 includes a first plate 104 and a pair of second plates 106 that are coupled to first plate 102 as shown best in FIG. 4. Ball nut 100 is fixed to first plate 102. A first roller 108, a second roller 110, and a third or upper roller 112 are coupled to each of plates 106 by axle pins 114, 116, 118, respectively, for rotation about axes 120, 122, 124, respectively.

Illustratively, first rollers 108 are offset transversely from respective second rollers 110 and upper rollers 112 are positioned to lie vertically above respective second rollers 110 as shown in FIGS. 3–6. In addition, pivot axis 118 of rollers 112 intersects axis 94 of threaded shaft and pivot axes 120, 122 of associated rollers 108, 110 each intersect axis 89 of hydraulic cylinder 76 as shown best in FIG. 4. Thus, vertical distance 115 between axis 89 and axis 94 is substantially equivalent to vertical distance 117 between axis 122 and axis 124. Optionally, axle pins 118 may include portions which couple plates 106 to plate 104. In addition, axle pin 116 preferably is configured as a single axle pin such that rollers 110 are coupled to end portions thereof and such that piston rod 80 is coupled to a middle portion thereof.

Figure 4:
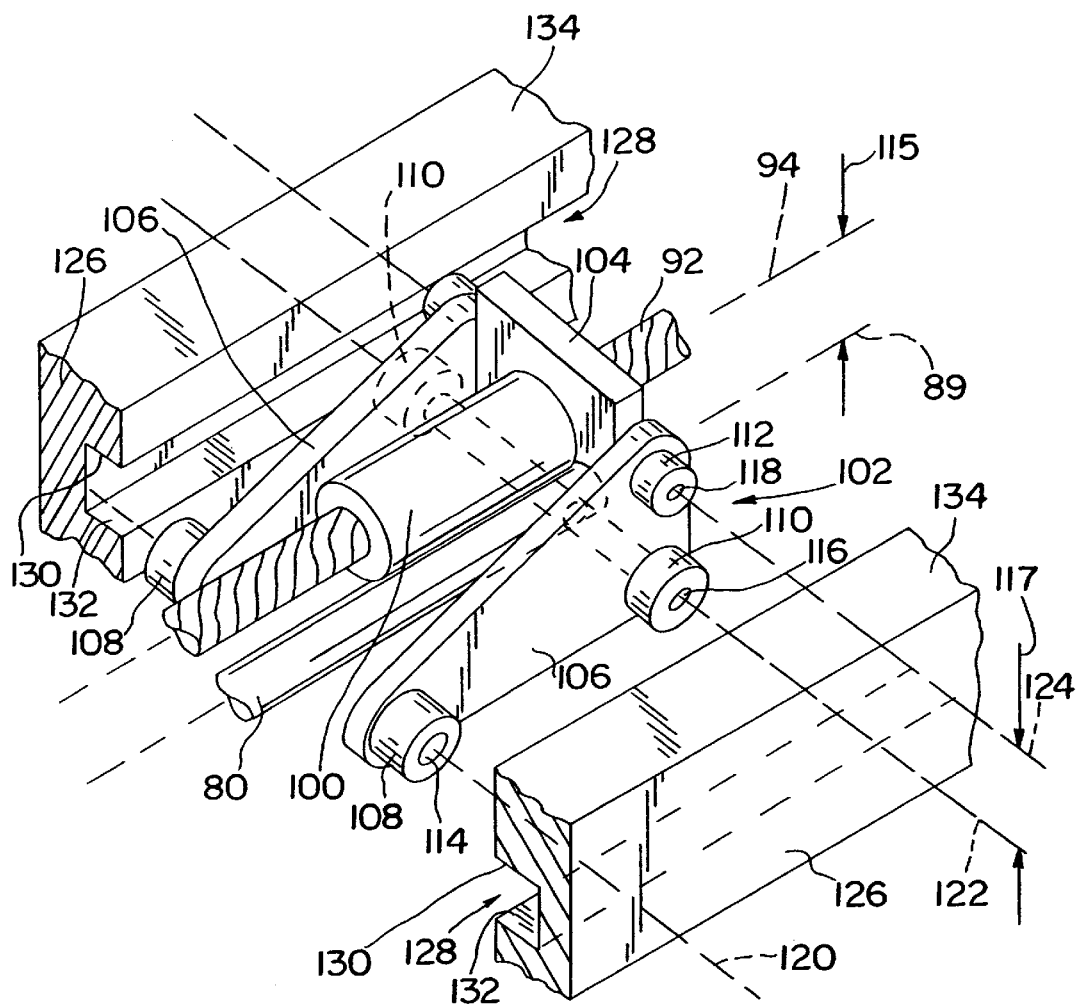
FIG. 4 is an exploded perspective view of the deck-slide mechanism, with portions broken away, showing details of the carriage assembly and showing portions of a pair of track members that guide the movement of the carriage assembly.

Transmission assembly 82 also includes a pair of track members 126, each of which is formed to include a slot or channel 128 as shown best in FIG. 4. Slot 128 defines a top track surface 130 and a bottom track surface 132. Rollers 108, 110 associated with each of plates 106 are received in slots 128 of respective track members 126. Each track member 126 includes an upper surface 134 upon which respective rollers 112 roll. The vertical spacing between track surfaces 130, 132 is only slightly larger than the diameter of rollers 108, 110 so that only a minimal amount of clearance exists between rollers 108, 110 and track surfaces 130, 132. Those skilled in the art will appreciate that each of rollers 108, 110 will engage only one of surfaces 130, 132 at any particular instance in time and that a small amount of clearance will exist between each of rollers 108, 110 and the other of surfaces 130, 132. Thus, track members 126 guide the movement of carriage assembly 102 during operation of deck-slide mechanism 52.

Figure 5:
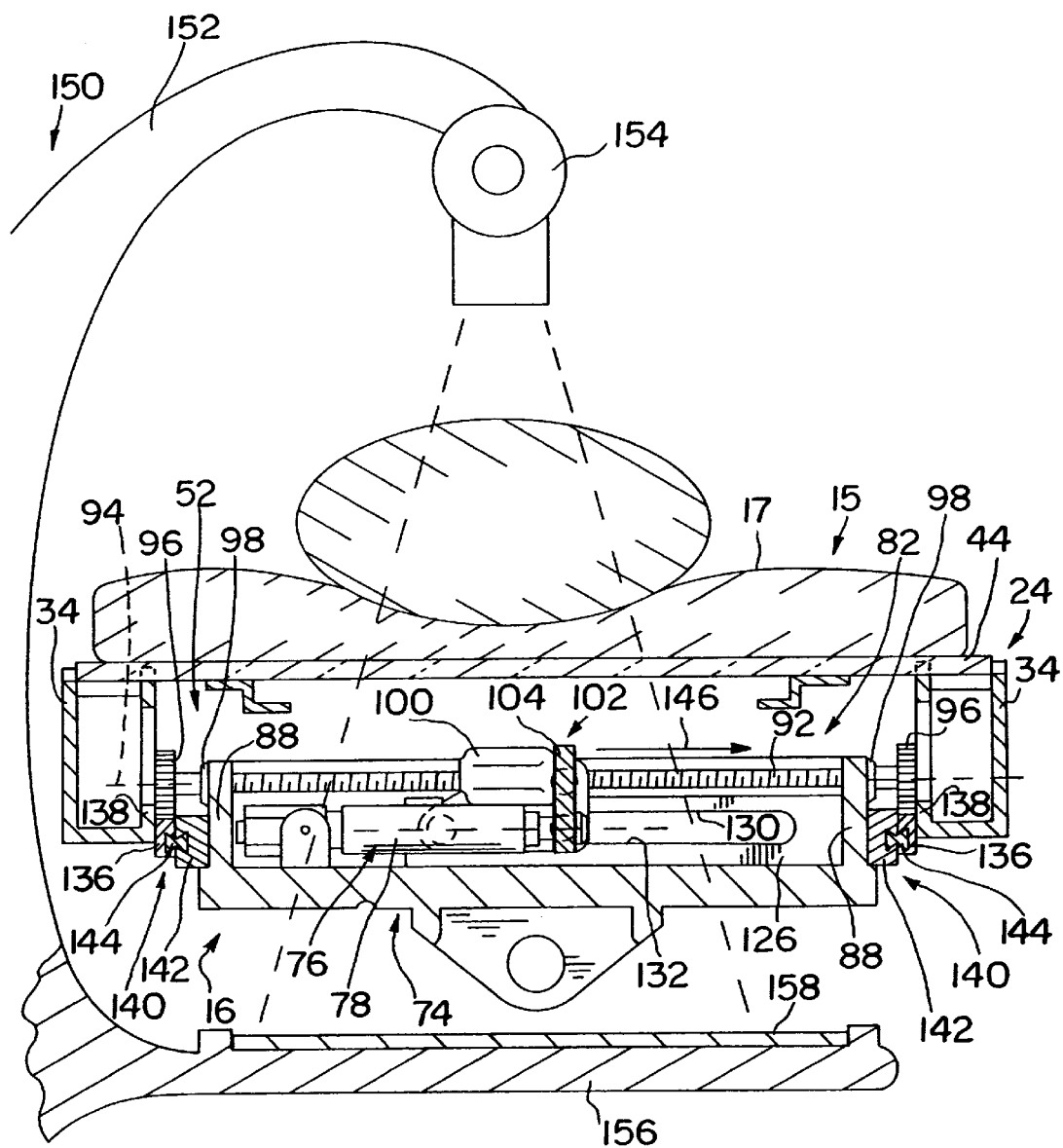
FIG. 5 is a sectional view taken along line 5—5 of FIG. 1 showing the piston rod of the hydraulic cylinder in a fully-retracted position having the ball nut positioned about half way between a right side and a left side of the patient-support deck and showing, diagrammatically, a C-arm imaging machine shooting an image of a patient supported by the patient-support deck.
Figure 6A:
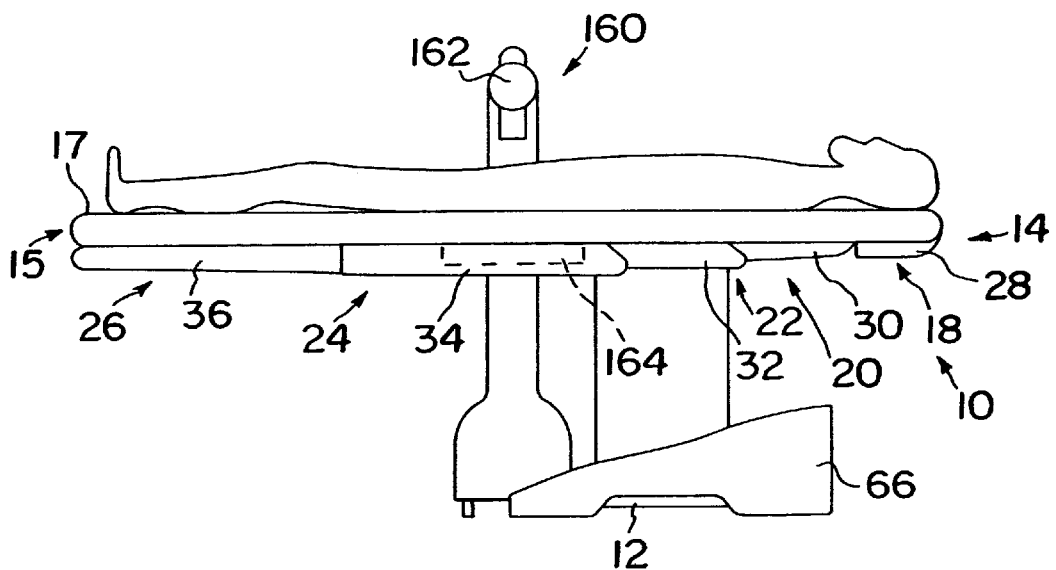
FIG. 6A is a side elevation view of the patient-support apparatus showing the patient-support deck moved to a rearwardmost position relative to the base and showing the X-ray imaging machine shooting an image of the patient.
Figure 6:
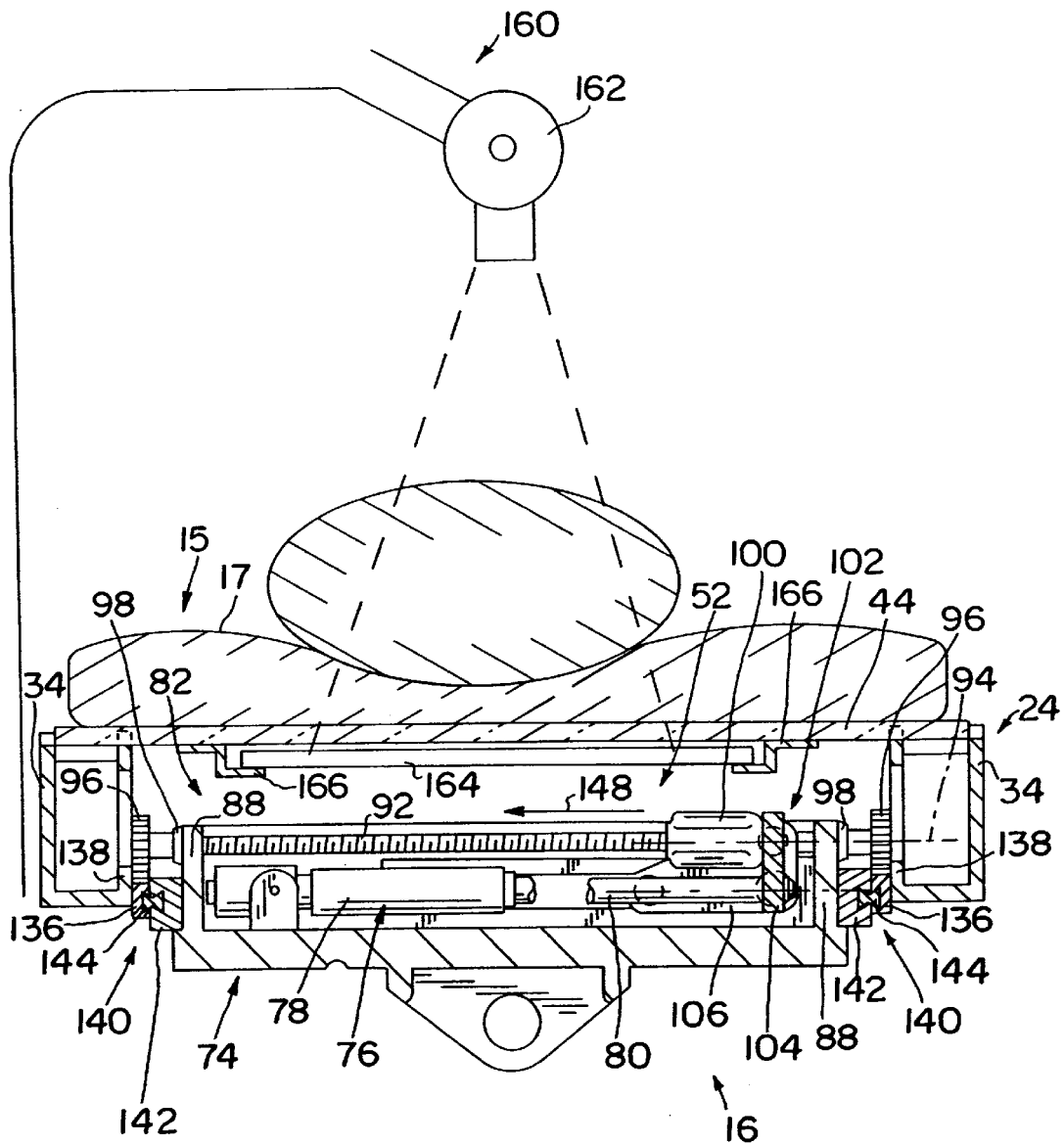
FIG. 6 is a sectional view similar to FIG. 5 showing the piston rod of the hydraulic cylinder in a fully-extended position having the ball nut positioned closer to the right side of the patient-support deck and showing, diagrammatically, an X-ray imaging machine shooting an image of a patient supported by the patient-support deck onto a cassette of film supported beneath a panel of the patient-support deck.

Transmission assembly 82 includes a pair of racks 136, each of which are coupled to respective vertical walls 138 of frame members 34 of seat section 24 as shown in FIGS. 3, 5 and 6. Pinions 96 each include a plurality of teeth 97 that engage associated teeth 137 of racks 136 in a conventional manner so that rotation of pinions 96 results in linear motion of racks 136. Deck-slide mechanism 52 includes a pair of linear bearings 140, each having a first member 142 coupled to platform 74 and a second member 144 coupled to a respective rack 136. Second member 144 slides relative to first member 142 when deck 14 moves longitudinally relative to base 12 and deck-positioning assembly 16. Thus, linear bearings 140 support deck 14 for longitudinal movement relative to deck-positioning assembly 16. Those skilled in the art will appreciate that other mechanisms, such as tracks and rollers or surface-to-surface contact between frame members 34 and platform 74, may be provided to support deck 14 for longitudinal movement relative to deck-positioning assembly 16. In addition, other options for the manner in which linear bearings 140 are coupled to platform 74 and to seat section 24 or racks 136 also will be readily apparent to those skilled in the art.

In use, hydraulic cylinder 76 is actuated either to extend or retract piston rod 80 relative to housing 78 thereby causing carriage assembly 102 either to move away from housing 78 in direction 146, shown in FIG. 5, or to move toward housing 78 in direction 148, shown in FIG. 6. As carriage assembly 102 moves, rollers 108, 110 roll within slot 128 relative to track members 126 and rollers 112 roll upon upper surfaces 134 of track members 126. Movement of carriage assembly 102 in directions 146, 148 causes ball nut 100 to move along axis 94 of shaft 92 in directions 146, 148, respectively. Because ball nut 100 is fixed to plate 104 of carriage assembly 102, ball nut 100 is constrained from rotating on shaft 92 and thus, movement of ball nut 100 along shaft 92 necessarily causes shaft 92 to rotate due to interaction between balls (not shown) of ball nut 100 and the threads of shaft 92. As shaft 92 rotates about transverse axis 94, pinions 96 also rotate about axis 94 causing longitudinal movement of racks 136 along with deck 14 which is coupled to racks 136.

When ball nut 100 moves in direction 146, shaft 92 and pinions 96 rotate in one direction and when ball nut 100 moves in direction 148, shaft 92 rotates in an opposite direction. Thus, the longitudinal direction of movement of deck 14 is dictated by the transverse direction of movement of ball nut 100. By having hydraulic cylinder 76, shaft 92, and track members 126 all transversely oriented, the longitudinal distance between side walls 86 of platform 74 can be kept to a minimum. In addition, the amount of longitudinal movement of deck 14 compared to the amount of transverse movement of ball nut 100 is dictated by the pitch of the threads of shaft 92 and the diameter of pinions 96. In a preferred embodiment of the present invention, five inches (12.7 cm) of transverse movement of ball nut 100 causes fourteen inches (35.6 cm) of longitudinal movement of deck 14. Thus, deck-slide mechanism 52 is packaged in a compact and efficient manner which provides imaging equipment with increased access for taking images of the portion of a patient supported on seat section 24.

It will be appreciated that it is within the scope of the present invention for mechanisms other than racks 136 and pinions 96 to be included in deck-slide mechanism 52 to convert rotation of shaft 92 into longitudinal movement of deck 14. For example, frictional contact between rollers mounted on shaft 92 and tracks mounted to seat section 24 could be employed in lieu of racks 136 and pinions 76. Those skilled in the art will also realize that sprockets mounted on shaft 92 and chains coupled to platform 74 and seat section 24 could be used as an alternative, as could pulleys mounted on shaft 92 and belts or cables coupled to platform 74 and seat section 24.

Figure 5A:
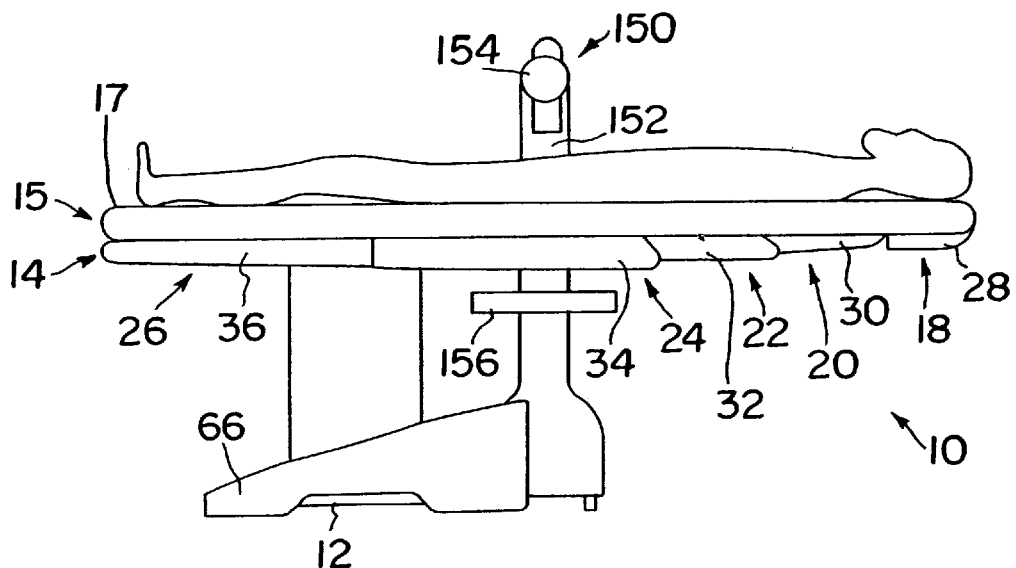
FIG. 5A is a side elevation view of the patient-support apparatus showing the patient-support deck moved to a forwardmost position relative to the base and showing the C-arm imaging machine shooting an image of the patient.

FIGS. 5 and 5A show a fluoroscopic imaging machine 150 having a C-arm 152 with a beam generator 154 above deck 14 and a tray 156 beneath deck 14. Tray 146 supports a film cassette 158 that captures fluoroscopic images of the portion of the patient supported thereabove. FIGS. 6 and 6A show an X-ray imaging machine 160 having a beam generator 162 above deck 14. A film cassette 164 that captures X-ray images of the portion of the patient supported thereabove is supported beneath panel 44 of seat section 24 by a pair of brackets 166 as shown in FIG. 6. Deck 14 is shown in its forwardmost position in FIG. 5A and deck 14 is shown in its rearwardmost position in FIG. 6A. Thus, by using deck-slide mechanism 52 to move deck 14 between the forwardmost and rearwardmost positions, C-arm 152 is able to take images of portions of the patient that would otherwise be inaccessible. In addition, moving deck 14 to either the forwardmost position or the rearwardmost position makes it easier for a caregiver to load film cassette 164 into the proper position beneath panel 44.

Patient-support apparatus 10 may include a user input device (not shown) of any conventional type that is used to command the operation of the drive mechanisms (not shown) included in patient-support deck 14 and included in deck-positioning assembly 16 and that is also used to command the operation of actuator 76 of deck-slide mechanism 52. Examples of user input devices that may be included in patient-support apparatus 10 are shown and described in U.S. patent application Ser. No. 09/187,825 which is assigned to the assignee of the present invention and which is hereby incorporated by reference herein.

Those skilled in the art will appreciate that deck-slide mechanism 52 can be employed in any patient-support device in which longitudinal movement of a patient-support deck relative to a base is desired, whether or not the patient-support deck also raises, lowers, or tilts. Therefore, the term "deck-positioning assembly" as used in the claims is intended to cover all types of-pedestal structures, frame assemblies, supports, and the like that may be used to couple a patient-support deck to a base.

A patient-support apparatus 210 includes a deck-positioning assembly 216 having an alternative embodiment deck-slide mechanism 252 as shown in FIGS. 7–10. Many components of patient-support apparatus 210 are substantially similar to like components of patient-support apparatus 10 and therefore, like reference numerals are used throughout to denote like components. Unlike deck-slide mechanism 52 which operates through actuator 76 and transmission assembly 82 to automatically move patient-support deck 14 longitudinally, deck-slide mechanism 252 operates to lock and unlock patient-support deck 14 for manual longitudinal sliding movement relative to base 12.

Figure 7:
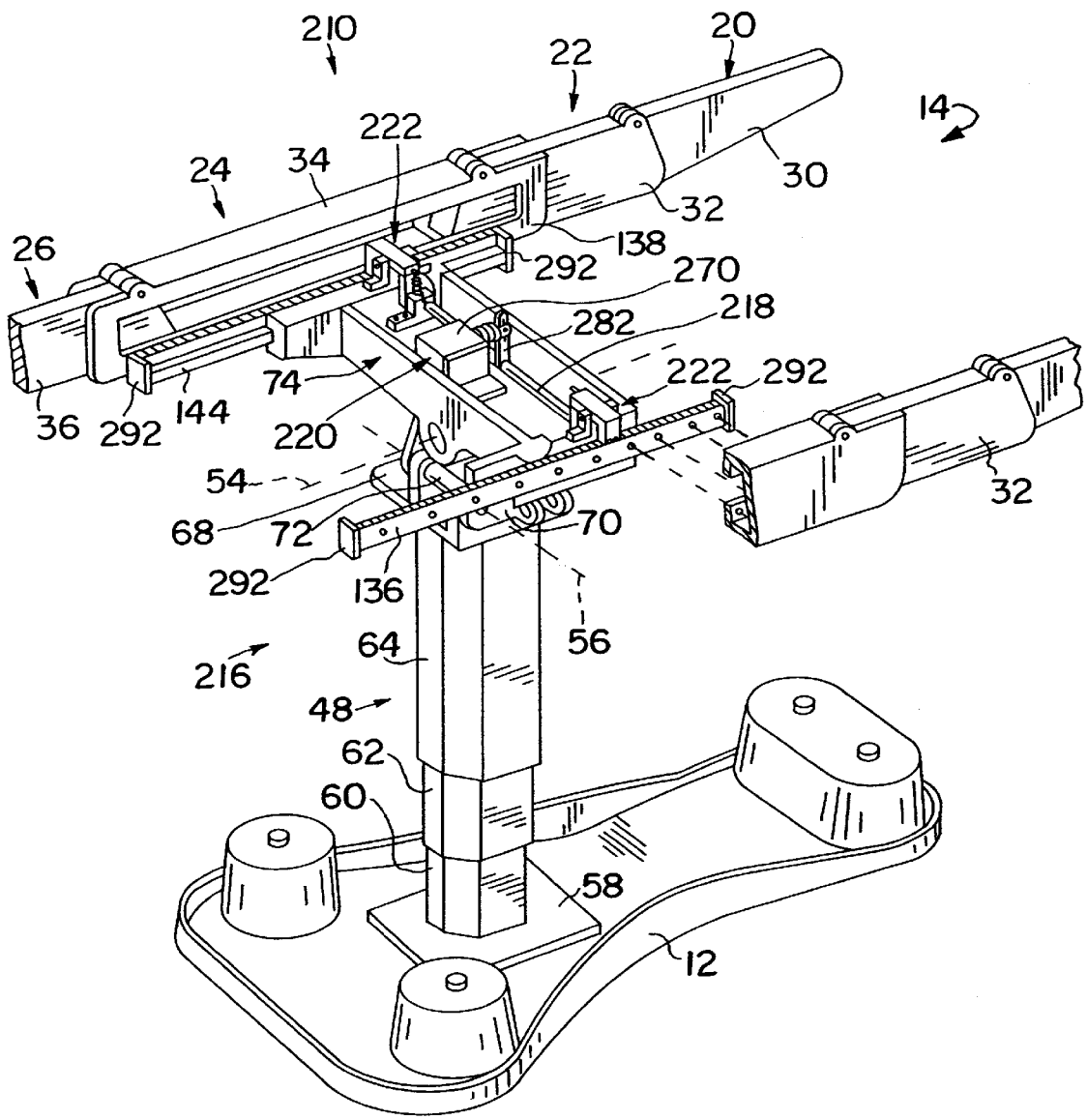
FIG. 7 is a perspective view, similar to FIG. 2, of an alternative embodiment patient-support apparatus in accordance with the present invention showing a base, a deck-positioning assembly including a hi/lo mechanism extending vertically upwardly from the base, a tilt/trend mechanism situated atop the hi/lo mechanism, and a deck-slide mechanism coupling the tilt/trend mechanism to the patient-support deck, the deck-slide mechanism including a lock assembly that operates to lock and unlock the patient-support deck for sliding movement relative to the base.
Figure 8:
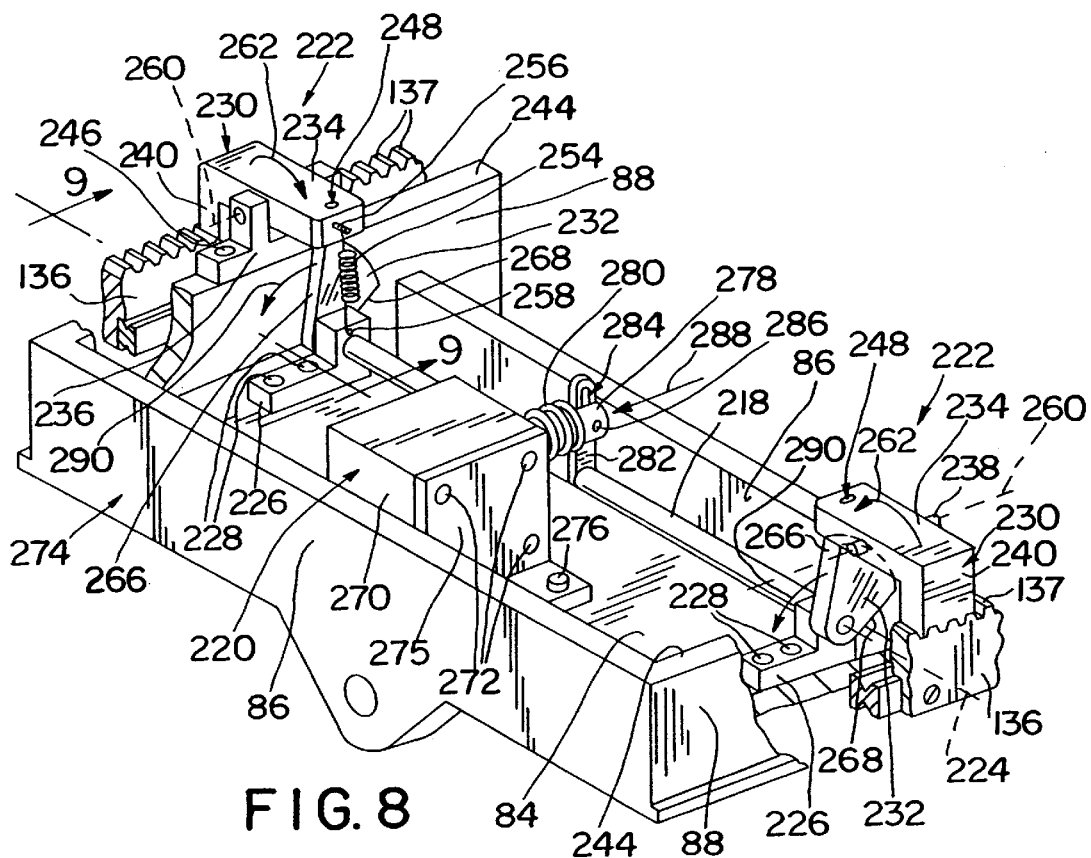
FIG. 8 is an enlarged perspective view of a portion of the patient-support apparatus of FIG. 7, with portions broken away, showing a shaft supported for rotation about a transverse axis relative to an upper platform of the tilt/trend mechanism, an actuator coupled to a link extending from the shaft, a pair of cams coupled to ends of the shaft, a pair of racks coupled to a seat section of the patient-support deck, a pair of linear bearings supporting the racks and patient-support deck relative to the upper platform, and a pair of pawls in a lock position engaging the respective racks to prevent longitudinal movement of the patient-support deck relative to the base.
Figure 9:
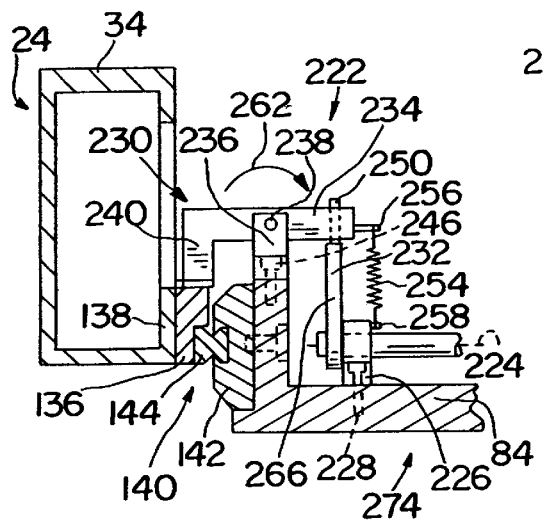
FIG. 9 is a sectional view taken along line 9—9 of FIG. 8 showing one of the pawls in the lock position.
Figure 10:
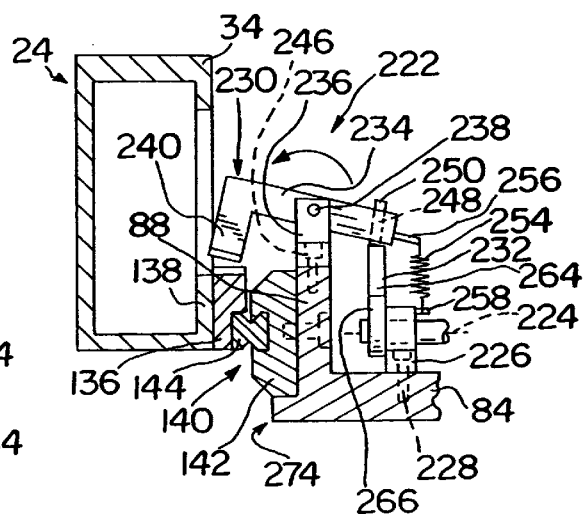
FIG. 10 is a sectional view, similar to FIG. 9, showing one of the pawls moved to an unlocking positioning disengaged from the respective rack to allow longitudinal movement of the patient-support deck relative to the base.

Deck-slide mechanism 252 includes a shaft 218, an actuator 220 that operates to rotate shaft 218 between first and second positions, and a pair of lock assemblies 222 coupled to shaft 218 as shown in FIG. 7. Shaft 218 is supported for rotation about a transverse axis 224 by a pair of brackets 226 that are coupled to bottom wall 84 of a platform 274 in any suitable manner such as by bolts 228 as shown in FIGS. 8–10. Each of the end portions of shaft 218 extend outwardly beyond respective brackets 226 but terminate between brackets 226 and the associated end walls 88 of platform 274. Illustratively, each bracket 226 is formed to include a bore that provides a plain bearing surface upon which shaft 218 rotates. Optionally, bearings or bushings (not shown) may be received within the bores of brackets 226 to support shaft 218 for rotation.

Lock assemblies 222 each include a member 230 that moves between a first or locking position, shown in FIGS. 7–9, and a second or unlocking position, shown in FIG. 10, in response to rotation of shaft 218 between its first and second positions. Each illustrated locking assembly 222 further includes a cam 232 coupled to the end portions of shaft 218 between the associated bracket 226 and wall 88 of platform 274. Cams 232 are fixed to shaft 218 to rotate therewith. In preferred embodiments, each member 230 is a pawl (hereinafter referred to as pawl 230) that is L-shaped having a first portion 234 coupled to a respective bracket 236 by a suitable coupler, such as a pin 238, and having a second portion 240 formed with one or more teeth 242 as shown best in FIG. 8. Brackets 236 are coupled to top surfaces 244 of end walls 88 in any suitable manner, such as by bolts 246. The first portion 234 of each pawl 230 is tapped with a threaded hole 248 and an adjuster or bolt 250 is threadedly received in hole 248. The lower end of each adjuster 250 is positioned to lie beneath first portion 234 of the respective cam 232 and is engaged by a cam surface 264 of the respective cam 232 as shown in FIGS. 9 and 10.

Lock assemblies 222 each include a spring 254 having an upper end coupled to first portion 234 of the respective pawl 230 in any suitable manner, such as by pin 256, and having a lower end coupled to the respective bracket 226 in any suitable manner, such as by pin 258. Pins 238 cooperate with brackets 236 to define respective longitudinal pivot axes 260 and springs 254 each act to bias pawls 230 to rotate about respective pivot axes 260 in the direction of arrows 262 shown in FIGS. 8 and 9. Of course, pawls 230 can only move in direction 262 when permitted to do so by movement of cams 232. Thus, springs 254 bias adjusters 250 into contact with cam surfaces 264 of respective cams 232. Cams 232 each include a long side 266 and a short side 268. Cam surfaces 264 smoothly arc between associated long sides 266 and short sides 268. As cams 232 rotate along with shaft 218 about axis 224, cam surfaces 264 wipe against the lower ends of adjusters 250 to change the position of pawls 230.

When pawls 230 are in the respective locking positions, adjusters 250 engage cam surfaces 264 closer to long sides 266 than short sides 268 of respective cams and teeth 242 engage teeth 137 of racks 136 thereby preventing racks 136 and patient-support deck 14 from moving longitudinally relative to base 12. Rotation of adjusters 250 fine tunes the position of pawls 230 relative to cams 232 to adjust the manner in which teeth 242 intermesh with teeth 137 when pawl 230 is in the locking position. When pawls 230 are in the respective unlocking positions, adjusters 250 engage cam surfaces 264 closer to short sides 268 than long sides 266 of respective cams 232 and teeth 242 are disengaged from teeth 137 of racks 136 which permits manual longitudinal movement of patient-support deck 14 relative to base 12.

Although illustrative lock assemblies 222 each include a pair of cams 232 that are coupled to shaft 218 and that move pawls 230 between the locking and unlocking positions, those skilled in the art will appreciate that mechanisms other than cams 232 can be employed in lock assemblies 222 without exceeding the scope of the present invention. For example, a pair of linkages coupling shaft 218 to respective pawls 218 could be included in lock assemblies 222 in lieu of cams 232. In addition, a cable or tether that is coupled to pawl 230 and that wraps around and unwraps from either shaft 218 or a pulley mounted on shaft 218 as shaft 218 rotates also would be within the scope of the present invention. Furthermore, sprockets mounted on shaft 218 could interact with chains coupled to respective pawls 230 to move pawls 230 between the locking and unlocking positions as shaft 218 rotates.

As previously described, deck-positioning assembly 216 includes an actuator 220 that operates to rotate shaft 218. Illustrated actuator 220 is an electric solenoid (hereinafter referred to as solenoid 220), although it is within the scope of the invention as presently perceived for any suitable device capable of causing rotation of shaft 218 to be included in deck-positioning assembly 216 in lieu of solenoid 220. Solenoid 220 includes a housing 270 that is coupled by suitable fasteners such as bolts 272 to a mounting bracket 275 which, in turn, is coupled by suitable fasteners such as bolts 276 to bottom wall 88 of platform 74 as shown in FIG. 8. Solenoid 220 also includes an output shaft 278 and a return spring 280 mounted on shaft 278. A portion of shaft 278 is situated inside housing 270 and a portion of shaft 278 is positioned to lie outside of housing 270.

A link 282 is fixed to a central portion of shaft 218 and extends perpendicularly therefrom as shown in FIG. 8. The distal end of link 282 is formed to include a slot 284. Output shaft 278 of solenoid 220 is coupled to link 282 by a pin 286, a middle portion of which is received in slot 284 and end portions of which are received in pin-receiving apertures formed in distal end portions of shaft 278 that lie on either side of link 282. When solenoid 220 is actuated in a conventional manner by applying an electric potential to leads (not shown) of solenoid 220, shaft 278 moves in the direction of arrow 288, shown in FIG. 8, such that shaft 278 retracts further into housing 270. Movement of shaft 278 in direction 288 causes link 282, shaft 218, and cams 232 to pivot about axis 224 in the direction of arrows 290, thereby permitting springs 254 to pivot pawls 230 about axes 260 in directions 262 from their respective locking positions to their respective unlocking positions.

When solenoid 220 is actuated moving shaft 278 in direction 288, pin 286 moves within slot 284 as link 282 rotates and, furthermore, link 282 compresses return spring 280 against housing 270. When solenoid 220 is deactuated by removing the electric potential from the leads thereof, spring 280 pushes against link 282 thereby rotating link 282, shaft 218, and cams 232 about axis 224 in a direction opposite to direction 288. Rotation of cams 232 about axis 224 in the direction opposite to direction 288 forces pawls 230 to move from the unlocking position, shown in FIG. 10, to the locking position, shown in FIG. 9. Additionally, rotation of link 282 in the direction opposite to direction 288 pulls pin 286 away from housing 270 of solenoid, thereby extending shaft 278 out of housing 270. Solenoid 220 is configured with conventional structure to limit the amount by which shaft 278 retracts into and extends out of housing 270. For example, complete compression of spring 280 or contact between shaft 278 and a first stop (not shown) inside housing 270 limits the retraction of shaft 278 into housing 270. In addition, contact between a shoulder (not shown) of shaft 278 and a second stop (not shown) inside housing 270 limits the extension of shaft 278 out of housing 270.

As previously described, when pawls 230 are moved to the respective unlocking positions, deck 14 is manually movable to change the longitudinal position of deck 14 relative to base 12. As deck 14 moves longitudinally, first members 142 of linear bearings 140 slide relative to second members 144. A set of stops or stop blocks 292, shown in FIG. 7, are provided for limiting the amount by which deck 14 may be longitudinally moved when pawls 230 are in the unlocking positions.

Figure 11:
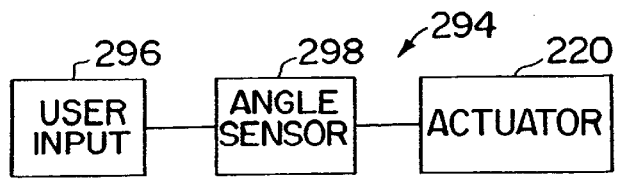
FIG. 11 is a block diagram of a portion of a control system for controlling the deck-positioning assembly of FIG. 7, showing a user input block, an angle sensor block, and an actuator block.

Patient-support apparatus 210 includes a control system that is used to command the operation of the various drive mechanisms (not shown) of deck-positioning assembly 216 and that is used to command the operation of actuator 220. An illustrative portion 294 of the control system associated with actuator 220 includes a user input 296 and an angle sensor 298 as shown diagrammatically in FIG. 11. User input 296 receives user input commands to lock and unlock each of lock assemblies 222 thereby controlling locking and unlocking of deck 14 relative to base 12. Angle sensor 298 is configured to sense whether seat section 24 is tilted about transverse axis 56. If seat section 24 is tilted in either direction about axis 56, then angle sensor 298 operates to disable actuator 220 from being actuated. If seat section 24 is in a horizontal position, as shown in FIG. 7, then angle sensor 298 operates to enable actuator 220 thereby permitting actuation of actuator 220. Disabling actuator 220 when seat section 24 is tilted about axis 56 enhances the safety of patient-support apparatus 210 because of the possibility that deck 14 would slide relative to platform 74 too rapidly if lock assemblies 222 were unlocked when seat section 24 is tilted.

Those skilled in the art will appreciate that many different types of angle sensors, such as mercury switches, potentiometers, rotary encoders, gravity-sensitive resistive devices, and the like may be employed in the control system of deck-positioning assembly 216 to sense the angle of seat section 24 and to disable or enable, as the case may be, actuator 220. Those skilled in the art will also appreciate that angle sensor 298 may be coupled to any one of frame members 34 of seat section 24, panel 44 of seat section 24, or platform 274 and still provide an output signal indicative of the angle of seat section 24. In addition, those skilled in the art will appreciate that it is within the scope of the invention as presently perceived for the output signal from angle sensor 298 to be coupled to additional circuitry that conditions and/or processes the output signal before enabling or disabling actuator 220.

Although the invention has been described in detail with reference to certain preferred embodiments, additional variations and modifications exist within the scope and spirit of the invention as described and defined in the following claims.

What is claimed is:

1. A patient-support apparatus comprising a base, a patient-support deck having a longitudinal length and a transverse width, and a deck-positioning assembly coupling the patient-support deck to the base, the patient-support deck being supported with respect to the deck-positioning assembly for longitudinal movement, the deck-positioning assembly including an actuator having a first portion and a second portion that moves transversely relative to the first portion, and the deck-positioning assembly including a transmission assembly configured to convert transverse movement of the second portion relative to the first portion into longitudinal movement of the patient-support deck relative to the base.

2. The patient-support apparatus of claim 1, wherein the actuator is a linear actuator and the second portion moves relative to the first portion along a first transverse axis.

3. The patient-support apparatus of claim 2, wherein the linear actuator is a hydraulic cylinder, the first portion is a housing of the hydraulic cylinder, and the second portion is a piston rod of the hydraulic cylinder.

4. The patient-support apparatus of claim 2, wherein the transmission assembly includes a ball nut and a threaded shaft, the ball nut is coupled to the second member of the linear actuator, the threaded shaft is supported for rotation about a second transverse axis, and the ball nut is coupled to the threaded shaft such that movement of the ball nut by the second member causes rotation of the threaded shaft.

5. The patient-support apparatus of claim 4, wherein the second transverse axis is positioned to lie vertically above the first transverse axis.

6. The patient-support apparatus of claim 1, wherein the transmission assembly includes a ball nut and a threaded shaft, the ball nut is coupled to the second member of the actuator, the threaded shaft is supported for rotation about a transverse axis, and the ball nut is coupled to the threaded shaft such that movement of the ball nut by the second member causes rotation of the threaded shaft.

7. The patient-support apparatus of claim 6, wherein the transmission assembly further includes a pinion coupled to the threaded shaft and a rack coupled to the patient-support deck, the pinion engages the rack.

8. The patient-support apparatus of claim 7, further comprising a linear bearing having a first member and a second member that slides relative to the first member, the first member is coupled to the deck-positioning assembly, and the second member is coupled to the rack.

9. A patient support apparatus comprising a base, a patient-support deck having a longitudinal length and a transverse width, a mattress supported by the patient-support deck and having an upwardly facing patient-support surface, a deck-positioning assembly coupling the patient-support deck to the base. the patient-support deck and mattress being supported with respect to the deck-positioning assembly for longitudinal movement, the deck-positioning assembly including a shaft having a transverse axis of rotation, a pinion coupled to the shaft, and a rack coupled to the patient-support deck, the pinion engaging the rack such that rotation of the shaft about the transverse axis longitudinally moves the patient-support deck and the mattress relative to the base, and a driver coupled to the shaft and actuatable to rotate the shaft, wherein the shaft is formed to include threads, the driver includes a ball nut mounted on the shaft in engagement with the threads so that axial movement of the ball nut along the shaft causes rotation of the shaft, and the driver includes a linear actuator coupled to the ball nut so that actuation of the linear actuator moves the ball nut axially along the shaft.

10. The patient-support apparatus of claim 9, wherein the linear actuator is a hydraulic piston and cylinder assembly.

11. The patient-support apparatus of claim 9, wherein the driver includes a carriage assembly coupling the linear actuator to the ball nut, the carriage assembly includes a plate coupled to the linear actuator and coupled to the ball nut, the carriage assembly includes a roller coupled to the plate, and the deck-positioning assembly includes a track member having a slot in which the roller is received.

12. The patient-support apparatus of claim 9, wherein the threads of the shaft are configured and the pinion is sized such that axial movement of the ball nut along the shaft by a first distance causes longitudinal movement of the patient-support deck and mattress by a second distance that is at least twice the first distance.

13. A patient-support apparatus comprising a base a patient-support deck having a longitudinal length and a transverse width.

a mattress supported by the patient-support deck and having an upwardly facing patient-support surface, a deck-positioning assembly coupling the patient-support deck to the base, the patient-support deck and mattress being supported with respect to the deck-positioning assembly for longitudinal movement, the deck-positioning assembly including a shaft having a transverse axis of rotation, a pinion coupled to the shaft, and a rack coupled to the patient-support deck, the pinion engaging the rack such that rotation of the shaft about the transverse axis longitudinally moves the patient-support deck and the mattress relative to the base, and a driver coupled to the shaft and actuatable to rotate the shaft, the driver being positioned beneath the shaft.

14. The patient-support apparatus of claim 13, wherein the patient-support deck includes a seat section having a head end and a foot end, at least one section coupled for pivoting movement to the seat section adjacent the head end thereof, at least one other section coupled for pivoting movement to the seat section adjacent the foot end thereof, and the rack is coupled to the seat section.

15. The patient-support apparatus of claim 14 wherein the seat section includes a longitudinally extending frame member having a vertical face and the rack is coupled to the vertical face.

16. The patient-support apparatus of claim 15, wherein the deck-positioning assembly includes a linear bearing and a platform, the linear bearing includes a first member and a second member that slides relative to the first member, the first member is coupled to the platform and the second member is coupled to the rack.

17. A patient-support apparatus comprising a base, a patient-support deck having a longitudinal length and a transverse width.

a mattress supported by the patient-support deck and having an upwardly facing patient-support surface, and a deck-positioning assembly coupling the patient-support deck to the base, the patient-support deck and mattress being supported with respect to the deck-positioning assembly for longitudinal movement, the deck-positioning assembly including a shaft having a transverse axis of rotation, a pinion coupled to the shaft, and a rack coupled to the patient-support deck, the pinion engaging the rack such that rotation of the shaft about the transverse axis longitudinally moves the patient-support deck and the mattress relative to the base, wherein the shaft is formed to include threads, the deck-positioning assembly includes a ball nut mounted on the shaft in engagement with the threads, axial movement of the ball nut along the shaft causes rotation of the shaft, the deck-positioning assembly includes an actuator coupled to the ball nut, the actuator includes a cylinder and a piston rod that extends and retracts relative to the cylinder along an axis that is parallel to the transverse axis, and movement of the piston rod relative to the cylinder moves the ball nut axially along the shaft to produce longitudinal movement of the patient-support deck and the mattress.

18. A patient-support apparatus comprising a base, a patient-support deck having a longitudinal length and a transverse width, and a deck-positioning assembly coupling the patient-support deck to the base, the patient-support deck being supported with respect to the deck-positioning assembly for longitudinal movement, the deck-positioning assembly including a threaded shaft supported for rotation about a transverse axis, a pinion coupled to the shaft, a rack coupled to the patient-support deck, the pinion engaging the rack, a ball nut coupled to the threaded shaft, and an actuator coupled to the ball nut and actuatable to move the ball nut axially along the threaded shaft to rotate the threaded shaft and pinion resulting in longitudinal movement of the patient-support deck relative to the base.

19. The patient-support apparatus of claim 18, wherein the deck-positioning assembly includes a carriage assembly coupling the ball nut to the actuator, the carriage assembly includes a first portion coupled to the ball nut and a second portion coupled to the actuator.

20. The patient-support apparatus of claim 19, wherein the second portion is coupled to the first portion by a pin having a longitudinal axis that intersects the transverse axis of the threaded shaft.

21. The patient-support apparatus of claim 20, wherein the deck-positioning assembly includes a track member and the carriage assembly includes a roller mounted on the pin and engaging the track member, the roller rolling relative to the track member as the ball nut moves axially along the threaded shaft.

22. The patient-support apparatus of claim 19, wherein the deck-positioning assembly includes a track member having a slot formed therein, the carriage assembly includes a first roller coupled to the second portion, the first roller is received in the slot, and the first roller rolls within the slot relative to the track member as the ball nut moves axially along the threaded shaft.

23. The patient-support apparatus of claim 22, wherein the carriage assembly includes a second roller coupled to the second portion and transversely space apart from the first roller, the second roller is received in the slot, and the second roller rolls within the slot relative to the track member as the ball nut moves axially along the threaded shaft.

24. The patient-support apparatus of claim 22, wherein the track member includes a top surface, the carriage assembly includes an upper roller coupled to the second portion, the upper roller rolls along the top surface as the ball nut moves axially along the threaded shaft.

25. The patient-support apparatus of claim 18, wherein the actuator is a linear actuator that extends and retracts along a second transverse axis that is parallel with the transverse axis of the threaded shaft.

26. The patient-support apparatus of claim 25, wherein the linear actuator is positioned to lie beneath the threaded shaft.

27. A patient-support apparatus comprising a base, a patient-support deck having a longitudinal length and a transverse width, and a deck-positioning assembly coupling the patient-support deck to the base, the patient-support deck being supported with respect to the deck-positioning assembly for longitudinal movement, the deck-positioning assembly including a shaft rotatable about a transverse axis between a first position and a second position, a rack coupled to the patient-support deck, and a lock assembly coupled to the shaft, the lock assembly including a member that moves in response to rotation of the shaft, the member engaging the rack when the shaft is in the first position to prevent longitudinal movement of the patient-support deck relative to the base, and the member being disengaged from the rack when the shaft is in the second position to allow longitudinal movement of the patient-support deck relative to the base.

28. The patient-support apparatus of claim 27, wherein the deck-positioning assembly includes an actuator for moving the shaft between the first and second positions.

29. The patient-support apparatus of claim 28, wherein the actuator is an electric solenoid.

30. The patient-support apparatus of claim 29, further comprising an angle sensor coupled to the deck-positioning assembly and configured to sense a position of at least a portion of the patient-support deck, the angle sensor generating a signal when the portion of the patient-support deck is in a non-horizontal position that prevents the actuator from moving the shaft out of the first position.

31. The patient-support apparatus of claim 27, wherein the lock assembly includes a cam coupled to the shaft to rotate therewith, the cam engages the member and moves the member during rotation of the shaft.

32. The patient-support apparatus of claim 31, wherein the lock assembly includes a spring arranged to bias the member into contact with the cam.

33. The patient-support apparatus of claim 31, wherein the member pivots about a longitudinal axis during rotation of the cam and shaft about the transverse axis.

34. The patient-support apparatus of claim 27, wherein the member is a pawl.

35. The patient-support apparatus of claim 34, wherein the rack includes a plurality of teeth and the pawl is configured to engage more than one of the plurality of teeth.

36. The patient-support apparatus of claim 34, wherein the pawl pivots about a longitudinal axis during rotation of the of the shaft about the transverse axis.

37. A patient-support apparatus comprising a base, a patient-support deck having a longitudinal length and a transverse width, and a deck-positioning assembly coupling the patient-support deck to the base, the patient-support deck being supported with respect to the deck-positioning assembly for longitudinal movement, the deck-positioning assembly including a member that is movable between a first position preventing longitudinal movement of the patient-support deck relative to the base and a second position allowing longitudinal movement of the patient-support deck relative to the base, the lock assembly further including a shaft rotatable about a transverse axis to move the member between the first position and the second position.

38. The patient-support apparatus of claim 37, wherein the deck-positioning assembly includes an actuator for rotating the shaft about the transverse axis.

39. The patient-support apparatus of claim 38, wherein the actuator is an electric solenoid.

40. The patient-support apparatus of claim 39, further comprising an angle sensor coupled to the deck-positioning assembly and configured to sense a position of at least a portion of the patient-support deck, the angle sensor generating a signal to disable the actuator when the portion of the patient-support deck is in a non-horizontal position to prevent the shaft from moving the member out of the first position.

41. The patient-support apparatus of claim 37, wherein the lock assembly includes a cam coupled to the shaft to rotate therewith, the cam engages the member and moves the member during rotation of the shaft.

42. The patient-support apparatus of claim 41, wherein the lock assembly includes a spring arranged to bias the member into contact with the cam.

43. The patient-support apparatus of claim 41, wherein the member pivots about a longitudinal axis during rotation of the cam and shaft about the transverse axis.

* * * * *